United States Patent [19]

Charleux

[11] Patent Number: 5,041,135
[45] Date of Patent: Aug. 20, 1991

[54] POSTERIOR CHAMBER INTRAOCULAR LENS

[75] Inventor: Jacques Charleux, Lyons, France

[73] Assignee: Laboratoires Domilens, Lyons, France

[21] Appl. No.: 228,884

[22] Filed: Aug. 4, 1988

[30] Foreign Application Priority Data

Aug. 5, 1987 [FR] France ................. 87 11340

[51] Int. Cl.$^5$ ................. A61F 2/16
[52] U.S. Cl. ................. 623/6
[58] Field of Search ................. 623/6

[56] References Cited

U.S. PATENT DOCUMENTS

| | | | |
|---|---|---|---|
| 4,280,232 | 7/1981 | Hummel | 623/6 |
| 4,412,359 | 11/1983 | Myers | 623/6 |
| 4,477,931 | 10/1984 | Kelman | 623/6 |
| 4,664,666 | 5/1987 | Barrett | 623/6 |
| 4,701,181 | 10/1987 | Arnott | 623/6 |
| 4,755,182 | 2/1988 | Holmes | 623/6 |
| 4,878,911 | 11/1989 | Anis | 623/6 |

FOREIGN PATENT DOCUMENTS

| | | | |
|---|---|---|---|
| 3140465 | 4/1983 | Fed. Rep. of Germany | 623/6 |
| 8500527 | 1/1986 | Netherlands | 623/6 |
| 2114315 | 8/1983 | United Kingdom | 623/6 |
| 2124500A | 2/1984 | United Kingdom | 623/6 |

Primary Examiner—Ronald Frinks
Attorney, Agent, or Firm—Browdy and Neimark

[57] ABSTRACT

An intraocular lens comprising a support part connected to a central part by a single attachment integral with the support part and the central part. The attachment is provided with a blind hole.

The support part is inclined relative to the central part in the direction of convexity of the central part.

The central part of the implant is in the shape of a meniscus.

4 Claims, 2 Drawing Sheets

POSTERIOR CHAMBER INTRAOCULAR LENS

FIELD OF THE INVENTION

This invention relates to a posterior chamber intraocular lens or implant of the intracapsular type, i.e., an implant intended to be put in place in the posterior chamber of the eye, on the inside of the capsule of the crystalline lens during removal of the latter as a result of a cataract.

BACKGROUND OF THE INVENTION

FIG. 1 represents, in cross section, the anterior part of an eyeball inside which an implant 10 of this type is placed.

As the figure shows, posterior chamber 5 is limited in front by iris 4 and in the back by ciliary body 7 and crystalline lens 6.

The anterior part of the eye further comprises cornea 1, pupil 2 and iris 4 delimiting between themselves anterior chamber 3.

As indicated above, intracapsular posterior chamber implant 10 is put in place inside the capsule, i.e., the investing membrane 6 of the crystalline lens, the latter being removed.

Implant 10 of known type, represented in cross section in FIG. 1, and in plan in FIG. 2, consists of central part 11 forming the lens itself and support part 12.

Central part is biconvex (cf. FIG. 2) and the support part consists of circular crown 13 coaxial with central part 11 and connected to the latter by two "bridges" located along the same diameter.

The circular shape of support part 12 of this implant makes possible a good centering of the latter in the posterior chamber of the eye.

Further, the annularly shaped space delimited between support crown 13 and central part 11 of the implant allows a better attachment of the latter in the capsule of the crystalline lens by "welding" between the two walls 6a, 6b of this capsule.

However, this implant has certain drawbacks. Actually, the presence of two diametral bridges gives it a certain rigidity not facilitating its placement.

Further, its biconvex shape favors the adherence to its two faces of the walls of the capsule of the crystalline lens. Because of this, in the case of secondary cataract, i.e., of the growth of cells opacifying the capsule of the crystalline lens after removal of the latter, the laser radiation used to destroy these cells also damages the surface of the lens to which they adhere.

SUMMARY OF THE INVENTION

The aim of this invention is to eliminate these drawbacks and to design an implant of said type which exhibits a great flexibility and is easy to put in place in the capsule of the crystalline lens and which makes it possible to solve satisfactorily the problems linked to a secondary cataract.

The object is achieved in the implant according to the invention, which is of the type consisting of a central part forming a lens and an elastic support part in the shape of a circular crown, in that the support part is connected to the central part by a single attachment formed in one piece with the support part and the central part and exhibiting a considerable width relative to that of the support part, and in that the support part is inclined relative to the central part.

This configuration gives the implant maximum flexibility by allowing it to be "folded" considerably in the attachment axis for its introduction into the capsule of the crystalline lens and therefore allowing the reduction of the incision necessary for its introduction. Once introduced into the capsule of the crystalline lens, the implant, thanks to its elasticity, extends and regains its circular shape to be housed correctly in the posterior chamber of the eye.

Centering and stability of the implant thus obtained are excellent, because the closed circular crown makes possible a 360° support inside the eye.

The fact that the support part is inclined relative to the central part makes it possible to "stretch" the membrane of the capsule on the implant and therefore to avoid any adherence of the latter to the central part of the latter.

According to an advantageous embodiment, the central part of the implant is in the shape of a meniscus, which makes it possible to avoid the adherence of the membrane of the capsule of the crystalline lens to this central part especially in the concave part of the latter. For this reason, in case of secondary cataract, the cells opacifying the membrane of the capsule can be destroyed by laser radiation without damaging the lens.

In any case, the invention will be better understood and other characteristics of the latter will be brought out with the following description with reference to the accompanying diagrammatic drawing illustrating a preferred embodiment.

DETAILED DESCRIPTION OF THE INVENTION

Figure 3:
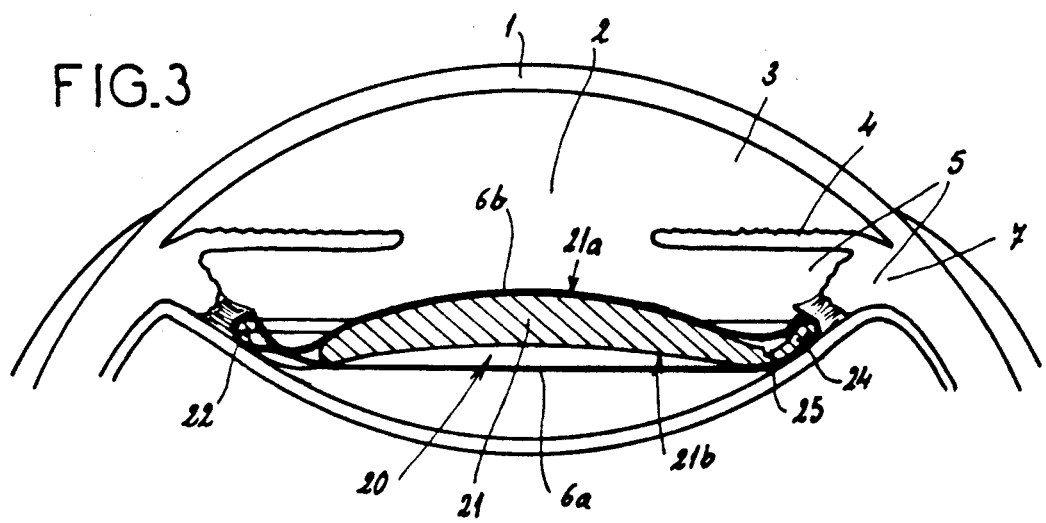
FIG. 3 is a view similar to FIG. 1 showing the implant according to the invention in place in the capsule of the crystalline lens.

FIG. 3 shows implant 20 according to the invention put in place inside capsule 6 of the crystalline lens.

Figure 4:
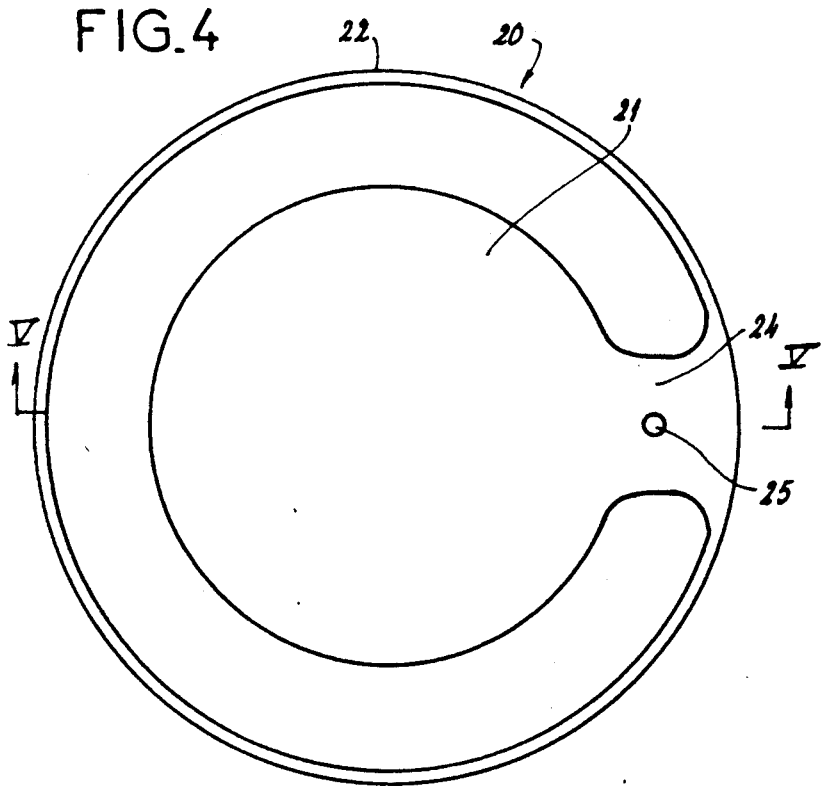
FIG. 4 is a plan view of the implant according to the invention.

As this figure and FIG. 4 show, this implant 20 consists of a central part 21 of circular shape constituting the lens itself and elastic support part 22.

Support part 22, like known implant 10, is in the shape of a circular crown.

However, unlike this known implant, it is attached to central part 21 by only a single attachment 24. This characteristic therefore gives the implant a flexibility and makes it possible to "fold" it to a maximum during its introduction into the eye.

Therefore this shape makes it possible to reduce to a maximum the incisions that have to be made in the cornea and capsule for putting the implant in place.

Figure 1:
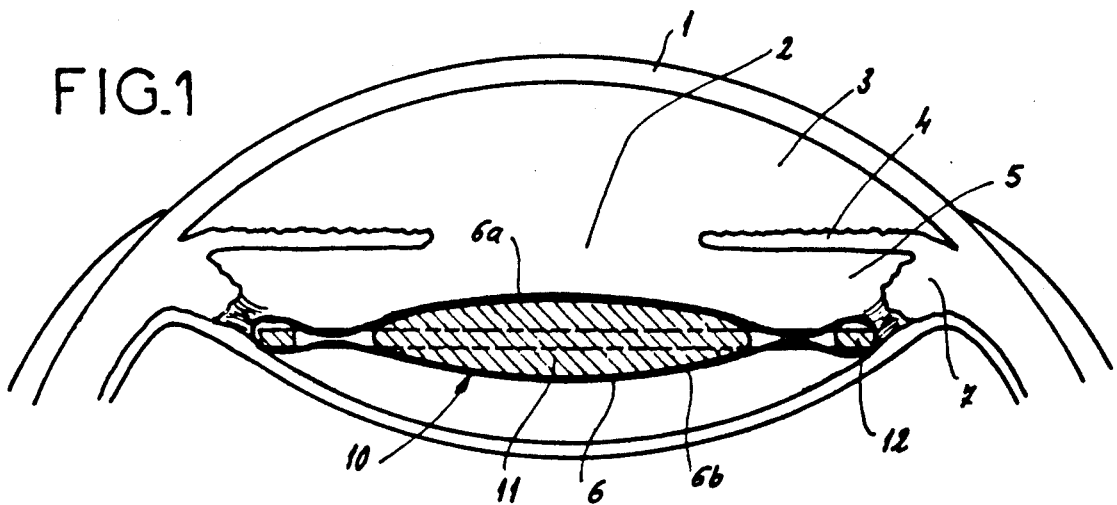
FIG. 1 represents the anterior part of the eyeball in cross-section.
Figure 2:
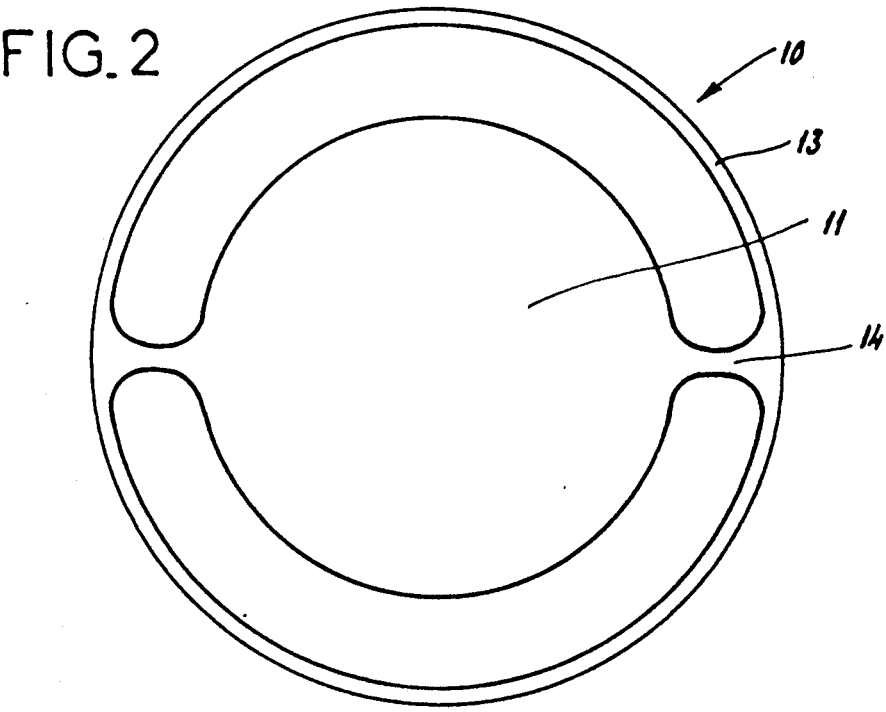
FIG. 2 is a plan view of an implant according to the prior art.

As the comparison of FIGS. 2 and 4 shows, attachment 24 of the implant according to the invention is much wider (about ten times wider) than each of attachments 14 of the known implant and, thereby, the implant according to the invention it much less fragile.

In this preferred embodiment, attachment 24 exhibits a width about ten times greater than that of support part 22, which constitutes a guarantee of its solidity.

Moreover, blind hole 25 is made in the central part of this attachment 24; this hole is intended to receive the end of a hook type instrument allowing a correct positioning of implant in the eye by the surgeon.

Figure 5:
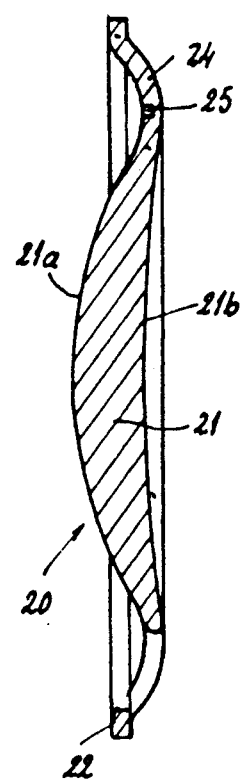
FIG. 5 is a view in section along V—V of FIG. 4.

As FIG. 5 shows, central part 21 of the implant is in the shape of a meniscus, i.e., it exhibits both a convex wall 21a and a concave wall 21b.

Moreover, the edges of the implant, i.e., support part 22 of the latter, is inclined relative to the central part in the direction of the convexity of the latter, i.e., in the direction of wall 21a.

Angle alpha, which support part 22 forms with general plane (P) of the lens, is equal to about 35°. This inclination of support part 22 relative to central part 21 has several advantages:

On the one hand, when the implant is folded for its introduction into the eye, this inclination and the curve of the central part, give the implant a capsule shape, facilitating its sliding inside the eye and removal of the membrane constituting capsule 6 of the crystalline lens.

This inclination of support part 22 makes it possible, on the other hand, to stretch the membrane constituting capsule 6 of the crystalline lens and particularly, as FIG. 3 shows, to stretch interior membrane 6a of the latter. In this way, concave face 21b of the implant is separated from the interior membrane 6a of the capsule and there is no contact between the latter.

This arrangement is advantageous in case of secondary cataract, i.e., opacification of the membrane of capsule 6 of the crystalline lens.

Actually, in such a case, the cells opacifying the membrane can be destroyed by laser radiation, without there being any danger of damage of wall 21b of the implant, because of the absence of contact between the latter and the membrane of the capsule of the crystalline lens.

Moreover, it will be noted that the circular shape of the implant according to the invention makes possible a good centering inside the eye and that the shape of the crown of its support part allows a better attachment of the latter inside the eye by "welding" between the two membranes 6a, 6b of the capsule of the crystalline lens in the spaces existing between central part 21 and support part 22 of the implant.

The angle α, which is formed with support part 22 with the general plan (P) of the lens is about 35°. This inclination of the support part 22 with respect to the central part 21 presents several advantages: firstly, since the lens is folded for insertion into the eye, this inclination of the support as well as the curvature if the central part, provide the implant with a capsular form, which facilitates its being slid into the interior of the eye and its being raised from the membrane which constitutes the capsule 6 of the crystalline lens.

This inclination of the support part 22 also enables stretching of the membrane constituting the capsule 6 of the crystalline lens and notably, as well as shown in FIG. 3, the stretching of the interior membrane 6a. In this manner, the concave face 21b of the implant is separated from the interior membrane 6a of the capsule and there is no other contact between them.

This arrangement is advantageous in the case of secondary cataracts, i.e., opacification of the capsule 6 of the crystalline lens.

It can be seen, incidentally, that the circular form of the implant according to the present invention permits a good centering in the interior of the eye and that the form of the corona of the support part permits a superior fixation of the lens in the interior of the eye by "soldering" between the two membranes, 6a, 6b, of the capsule of the crystalline lens in the interval existing between the central part 21 and the support part 22 of the implant.

It goes without saying that the present invention is not limited to the non-limiting example described above.

According to another embodiment of the present invention, the central part forming the lens can be biconvex in shape in a manner conforming to the form of the natural crystalline lens.

Advantageously, the angle of inclination of the support part with respect to the central part is approximately 20°.

In addition, the ratio of the radius of the front face to the radius of the rear face of this central part is about ½, which is very close to the geometry of the natural crystalline lens.

Of course, the invention is not limited to the single embodiment described above by way of nonlimiting example; rather, it takes in all embodiments using similar or equivalent means.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A posterior chamber intraocular implant comprising:
   a central part in the shape of a meniscus, said central part forming a lens, said lens having a front face and a rear face;
   an elastic support in the shape of a circular crown, said elastic support disposed coaxially with said central part so as to lie in a plane parallel to the plane of said central part, said support having an anterior face and a posterior face;
   said implant having only a single attachment lying radially to said lens and support, said single attachment formed integrally with said support and said central part, said attachment having a width substantially greater than the width of said support, said attachment being inclined relative to said elastic support so as to permit folding of said implant for introduction into the capsule of a crystalline lens of the eye.

2. An implant according to claim 1 wherein the attachment is provided with a blind hole.

3. An implant according to claim 1 wherein the attachment is inclined relative to said circular crown at about 35°.

4. An implant according to claim 1 wherein the attachment is inclined relative to said circular crown at about 20°.

* * * * *